United States Patent
Chong et al.

(10) Patent No.: US 12,312,575 B1
(45) Date of Patent: May 27, 2025

(54) CLOSED-LOOP PERFUSION CIRCUIT FOR CELL AND TISSUE CULTURES

(71) Applicant: CCLabs Pty Ltd, Melbourne (AU)

(72) Inventors: Hon Weng Chong, Toorak (AU); Chew Ling Lau, Melbourne (AU); Andrew Doherty, Melbourne (AU)

(73) Assignee: CCLabs Pty Ltd, Melbourne (AU)

( * ) Notice: Subject to any disclaimer, the term of this patent is extended or adjusted under 35 U.S.C. 154(b) by 0 days.

(21) Appl. No.: 18/405,694

(22) Filed: Jan. 5, 2024

Related U.S. Application Data

(62) Division of application No. 16/917,742, filed on Jun. 30, 2020, now Pat. No. 11,898,135.

(Continued)

(51) Int. Cl.
| | |
|---|---|
| *C12M 1/00* | (2006.01) |
| *C12M 1/04* | (2006.01) |
| *C12M 1/12* | (2006.01) |
| *C12M 1/32* | (2006.01) |
| *C12M 1/34* | (2006.01) |

(Continued)

(52) U.S. Cl.
CPC ............ *C12M 29/10* (2013.01); *C12M 21/08* (2013.01); *C12M 23/12* (2013.01); *C12M 23/16* (2013.01); *C12M 23/24* (2013.01); *C12M 23/34* (2013.01); *C12M 23/40* (2013.01); *C12M 23/58* (2013.01); *C12M 25/14* (2013.01); *C12M 29/04* (2013.01); *C12M 41/36* (2013.01)

(58) Field of Classification Search
CPC ...... C12M 29/10; C12M 21/08; C12M 23/12; C12M 23/16; C12M 23/24; C12M 23/34; C12M 23/40; C12M 23/58; C12M 25/14; C12M 29/04; C12M 41/36
See application file for complete search history.

(56) References Cited

U.S. PATENT DOCUMENTS

| | | |
|---|---|---|
| 5,459,069 A | 10/1995 | Palsson |
| 6,667,172 B2 | 12/2003 | Janigro |

(Continued)

FOREIGN PATENT DOCUMENTS

WO 2008124229 A2 10/2008

OTHER PUBLICATIONS

Jimbo, Y. et al. "Strengthening of Synchronized Activity by Tetanic Stimulation in Cortical Cultures: Application of Planar Electrode Arrays," IEEE Transactions on Biomedical Engineering, vol. 45, No. 11, Nov. 1998, pp. 1297-1304.

(Continued)

*Primary Examiner* — Liban M Hassan
(74) *Attorney, Agent, or Firm* — Lowenstein Sandler LLP

(57) ABSTRACT

A closed-loop perfusion system may include a sealed biological culture container configured to house a biological cell culture, and a filtering unit that permits passage of waste products from an output of the sealed biological cell culture container, permits passage of nutrients from a nutrient media solution, and blocks passage of beneficial molecules from the output of the sealed biological cell culture container. The system may further include a first fluid path between an output of the sealed biological cell culture container and an input of the filtering unit, a second fluid path between an output of the filtering unit and an input of the sealed biological cell culture, and a pump to control the flow of media through the first fluid path and the second fluid path.

18 Claims, 9 Drawing Sheets

Related U.S. Application Data

(60) Provisional application No. 62/869,400, filed on Jul. 1, 2019.

(51) Int. Cl.
*C12M 3/00* (2006.01)
*C12M 3/06* (2006.01)

(56) References Cited

U.S. PATENT DOCUMENTS

| | | |
|---|---|---|
| 6,875,605 B1 | 4/2005 | Ma |
| 9,861,810 B2 | 1/2018 | Anikeeva |
| 2001/0024821 A1 | 9/2001 | Potter |
| 2004/0131998 A1 | 7/2004 | Marom |
| 2006/0019385 A1 | 1/2006 | Smith |
| 2006/0094001 A1 | 5/2006 | Torre |
| 2013/0096922 A1 | 4/2013 | Asaei |
| 2014/0107446 A1 | 4/2014 | Tolosa |
| 2014/0222103 A1 | 8/2014 | Lauritzen |
| 2014/0279772 A1 | 9/2014 | Pennewitz |
| 2014/0287451 A1 | 9/2014 | McFetridge |
| 2015/0019140 A1* | 1/2015 | Downey .............. G01N 27/221 702/21 |
| 2015/0118745 A1 | 4/2015 | Iwamoto |
| 2015/0276707 A1 | 10/2015 | Lynch |
| 2016/0116459 A1 | 4/2016 | Mangan |
| 2017/0087766 A1 | 3/2017 | Chung |
| 2017/0192793 A1 | 7/2017 | Chilimbi |
| 2017/0316311 A1 | 11/2017 | Pilly |
| 2017/0337473 A1 | 11/2017 | Bernert |
| 2018/0101742 A1 | 4/2018 | Burge |
| 2018/0149639 A1 | 5/2018 | Pan |
| 2018/0169403 A1 | 6/2018 | Park |
| 2019/0034111 A1 | 1/2019 | Catthoor |
| 2019/0087713 A1 | 3/2019 | Lamb |
| 2020/0055041 A1 | 2/2020 | Kim |
| 2021/0143965 A1 | 5/2021 | Perotti |
| 2021/0334657 A1 | 10/2021 | Jordan |

OTHER PUBLICATIONS

Lin et al., "On-line observation of cell growth in a three-dimensional matrix on surface-modified microelectrode arrays", Biomaterials, 2009, 3110-3117, vol. 30, Elsevier.

* cited by examiner

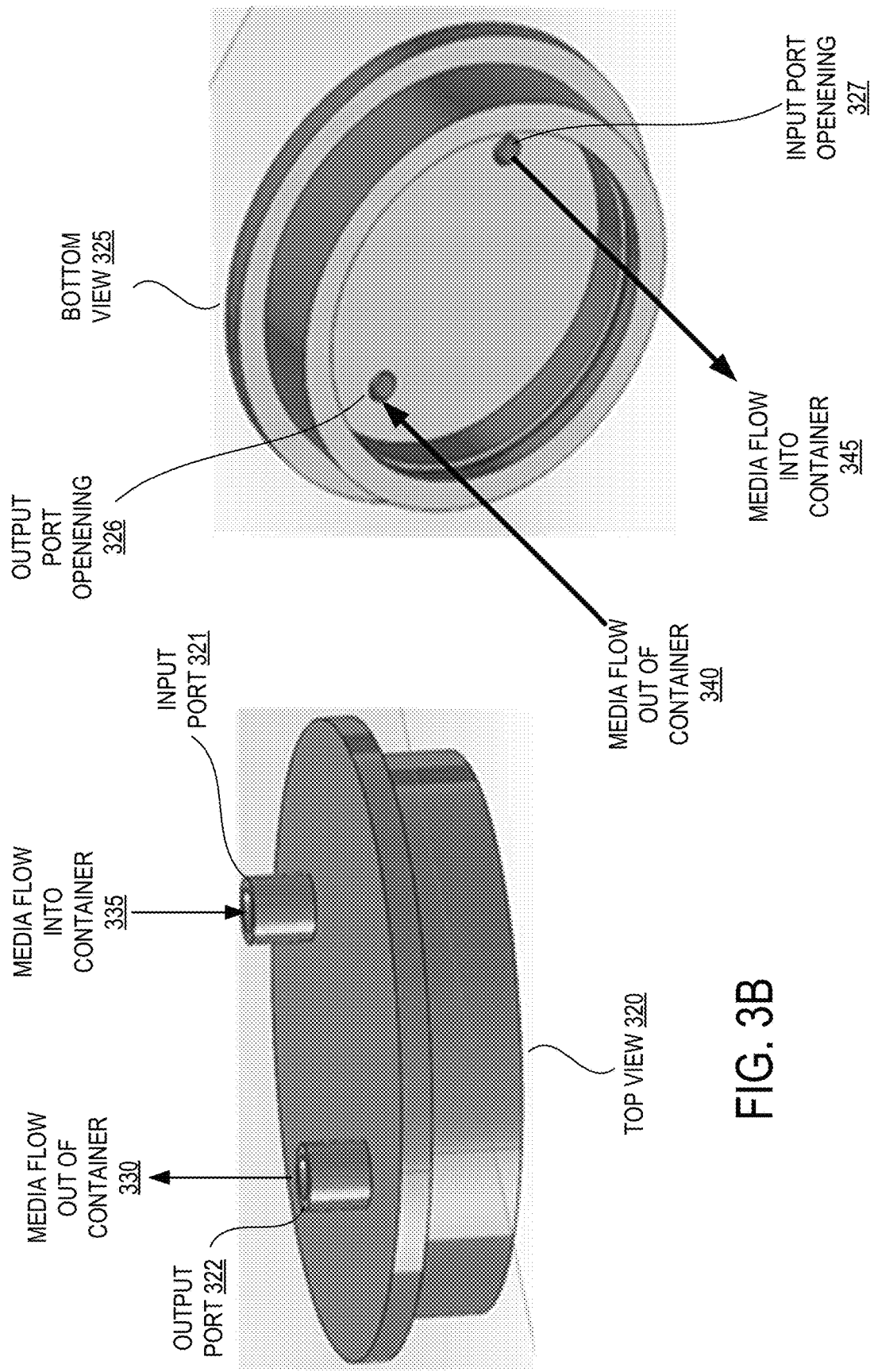

US 12,312,575 B1

CLOSED-LOOP PERFUSION CIRCUIT FOR CELL AND TISSUE CULTURES

RELATED APPLICATIONS

This patent application is a division of U.S. Non-Provisional application Ser. No. 16/917,742, filed Jun. 30, 2020, which claims the benefit under 35 U.S.C. § 119 (e) of U.S. Provisional Application No. 62/869,400, filed Jul. 1, 2019, all of which are herein incorporated by reference herein in their entireties.

TECHNICAL FIELD

Embodiments of the present disclosure relate, in general, to a closed-loop perfusion circuit for cell and tissue cultures.

BACKGROUND

Cell culture refers to the removal of cells from a plants or animals (or other living organisms) and subsequently growing the cells under artificial conditions in a laboratory environment. Cell culture is a major tool used in cellular and molecular biology that can provide a model system for studying the physiology, behavior, and biochemistry of cells, and the effects of pharmaceutical compounds (e.g., vaccines or therapeutics) and/or toxic compounds on cells. An artificial environment in which cells are cultured often includes a culture container that regulates the physicochemical environment (pH, osmotic pressure, temperature, etc.), and a nutrient media solution that supplies nutrients (amino acids, carbohydrates, vitamins, minerals, etc.), growth factors, hormones, and gases ($O_2$, $CO_2$, etc.).

Cells are generally maintained in an aqueous media. Cells in a culture container can be maintained by feeding them fresh nutrients on a periodic basis and removing accumulated waste products. The conventional process to feed cell cultures and remove waste byproducts produced by the cells is to open the culture container, draining all/half of the aqueous media from the culture container, and adding a replacement liquid media that includes fresh nutrients. This process can be prone to inefficiency and/or be harmful to cultures since continued replacement of liquid media can result in disruptive changes to the osmotic conditions in the container over the lifespan of the cells and/or tissues. Additionally, opening the culture container exposes the cell culture to an outside environment, which can result in environmental fluctuations that can negatively impact health of the cells and can lead to contaminations and/or infections. Furthermore, cell cultures often produce beneficial products as well, and removing half of the aqueous solution to remove metabolic waste causes roughly half of those beneficial products to be removed from the cell container. Furthermore, the manual process of opening the cell container, removing some portion of the aqueous media and adding some portion of a fresh aqueous media is a labor and time intensive task that increases the cost of cell research.

BRIEF DESCRIPTION OF THE DRAWINGS

The embodiments described herein will be understood more fully from the detailed description given below and from the accompanying drawings, which, however, should not be taken to limit the application to the specific embodiments, but are for explanation and understanding only.

FIGS. 3B-3C illustrate views of an alternate embodiment of a flat lid for a culture dish, in accordance with one embodiment.

DETAILED DESCRIPTION OF THE PRESENT INVENTION

Figure 1:
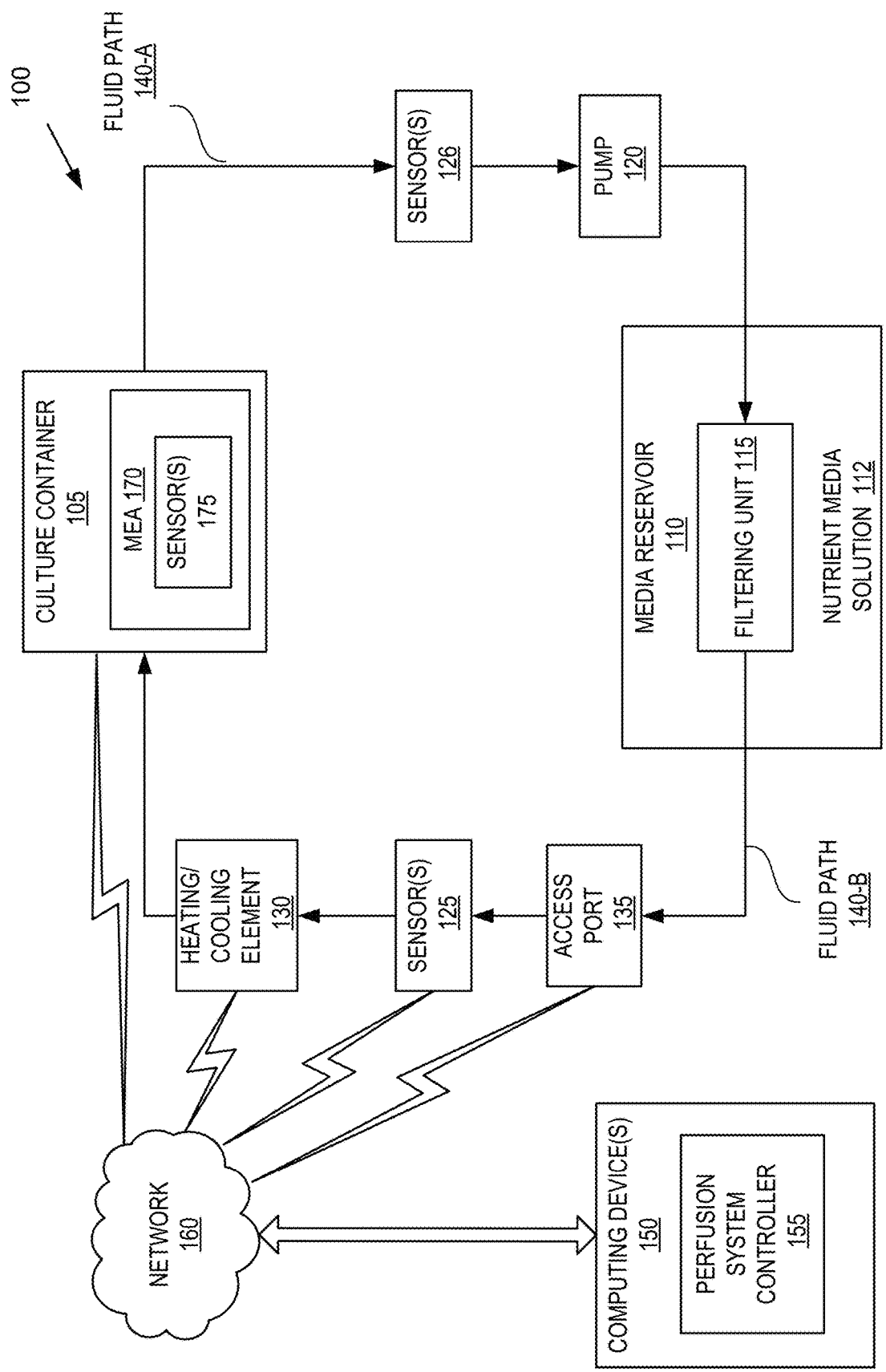
FIG. 1 illustrates an example system architecture for a closed-loop perfusion system, in accordance with one embodiment.

Described herein are embodiments of a closed-loop perfusion system for biological cell cultures. In one embodiment, the closed-loop perfusion system includes a sealed biological culture container configured to house a biological cell culture. The culture container is connected to a filtering unit. The filtering unit is connected to a media reservoir that contains a fresh nutrient media solution. The filtering unit may be disposed within the media reservoir or externally connected to the reservoir. The culture container and filtering unit are connected by two fluid paths that are made up of spans of tubing and multiple one-way valves to control the direction of flow of nutrient media solution within the system. The first fluid path connects the output of the culture container to an input of the filtering unit and the second fluid path connects the output of the filtering unit to the input of the culture container. The filtering unit includes a semi-porous membrane (e.g., a semi-permeable membrane) that permits the removal of metabolic waste from the closed-loop system while retaining any beneficial molecules produced by the cell culture within the system. In embodiments, fresh nutrients may diffuse into the closed-loop circuit, while waste products such as metabolic waste may diffuse out of the closed-loop circuit. Thus, the closed-loop perfusion system as described herein can allow the removal of metabolic waste from the loop and the delivery of fresh nutrients to a biological cell culture housed within the system more efficiently without exposing it to any outside environmental factors that can compromise cell health.

Conventional cell cultures are maintained in incubators in order to regulate their environment with respect to humidity, gas, and pH levels. These systems, however, often requires constant opening and closing of the incubator to refresh media in the cell culture container or examine the state of the cell culture, which is often not optimal for cell growth. In such instances, fresh air from the outside environment may enter the incubator that can cause fluctuation in the gas composition in the environment, which can lead to oxidative stress in the environment, causing cellular death. Changes in gas composition can also cause changes in pH and/or temperature, which can lead to mutation. There is also a risk that airborne pathogens may be present in the ambient air that may enter the incubator, causing infection, or cellular death. Similarly, repeated opening and closing of the incubator can cause fluctuations in the environment of the cells (e.g., changes in temperature and gas composition), which can result in inconsistency in cell growth. Moreover, in conventional systems, cell cultures are fed new nutrient media solution by replacing a portion of the solution already present in the culture container with fresh media. While this method can remove waste products from the media in the culture container, it can also result in the removal of beneficial molecules generated by the cell culture that are essential for healthy cell growth such as growth factors and hormones. Additionally, this can also result in changes in osmotic pressure in the media due to evaporation.

The closed-loop perfusion system in embodiments of the present disclosure can remedy the above and other deficiencies by sealing off the biological cell culture from external environmental factors that may negatively impact cell growth. Thus, a self-contained environment may be maintained in the closed-loop that can significantly improve cell growth and extend cell life within the culture container. Additionally, by utilizing a semi-porous membrane in the filtering unit, fresh nutrients can be added to the closed-loop and undesired products removed from the closed-loop without exposing the contents of the cell culture container to the outside environment. In some implementations, the undesired products may be metabolic waste produced by the cells, or other molecules produced by the cells that may be selectively removed according to their molecular weight size. Moreover, the semi-porous membrane can be configured or fabricated with pores sized to prevent loss of any beneficial molecules produced from the culture. For example, the porous membrane can be fabricated with pores of a desired size to selectively retain molecules according to their molecular weight size. Thus, fresh nutrient media solution may be provided to the culture without incurring the loss of any growth factors or hormones already produced. As such, the overall stability of the culture environment can be dramatically improved, and the life of the cells increased.

Additionally, the closed-loop perfusion system may be an automatic system (e.g., a continuously operating system) in embodiments. The system may continuously or periodically pump out stale aqueous media and at the same time pump in fresh aqueous media with minimal user intervention or input. This may have the double benefit of reducing an amount of time that a technician spends maintaining cell cultures and increasing the availability of fresh nutrients to the cell cultures.

FIG. 1 illustrates an example system architecture for a closed-loop perfusion system 100, in accordance with one embodiment. As shown, the closed-loop perfusion system 100 includes a culture container 105, a filtering unit 115, a media reservoir 110, a fluid path 140-A between the culture container 105 and the filtering unit 115, and a fluid path 140-B between the filtering unit 115 and culture container 105. In one embodiment, filtering unit 115 may be disposed within the media reservoir 110. Alternatively, filtering unit 115 may be externally connected to media reservoir 110. In some implementations, the closed-loop perfusion system 100 may also include one or more additional components coupled to the fluid paths 140-A and 140-B as described in further detail below.

Culture container 105 may be a sealed biological culture container configured to house a biological cell culture. The biological cell culture can include plant or animal cells for the purposes of growing the cells under artificial conditions. For example, the biological cell culture in culture container 105 can include neural cells. In some implementations, the culture container 105 can include a dish that holds the biological cell culture and a lid that is attached to the dish to form a water-tight seal. For example, the lid may be affixed to the dish using an O-ring, a rubber gasket, or other similar material to prevent contaminants from entering the container and to prevent the contents of the container from leaking out. Culture container 105 may additionally include an input port to allow media to flow into the container and an exit port to allow media to exit the container. In some implementations, the lid of culture container 105 may be flat. Alternatively, the lid of culture container 105 may be a transparent lid with a concave portion that is configured to receive a camera to enable images to be generated of the contents of culture container 105. Various embodiments of the lid of culture container 105 are described in further detail below with respect to FIGS. 3A-3D.

As noted above, closed-loop perfusion system 100 additionally includes a filtering unit 115 that is disposed within a media reservoir 110. In embodiments, the media reservoir 110 contains a nutrient media solution 112 that is circulated through the closed-loop perfusion system 100 to feed the biological cells in the culture container 105 as described herein. In some implementations, the nutrient media solution 112 can include trophic growth hormone factor for the biological culture (e.g., neurotrophins, ciliary neurotrophic factors (CNTF), glial cell line derived neurotrophic factors (GDNF), ephrins, epidermal growth factors (EGF), transforming growth factors (TGF), or neuron derived neurotrophic factors (NDNF)), a basal media (e.g., an inorganic salt, an amino acid, an energetic substrate, a vitamin, a pH buffer, or a pH indicator), and/or a supplement (e.g., a vitamin, a protein, a hormone steroid, a hormone thyroid, an essential fatty acid, a lipid, a sulfate mineral, an organic chemical compound, a monosaccharide, or a nucleotide).

As noted above, filtering unit 115 can be submerged in the nutrient media solution 112 within media reservoir 110. Alternatively, filtering unit 115 can be externally connected to media reservoir 110. In some implementations, filtering unit 115 includes a semi-porous membrane that facilitates the flow of molecules in solution based on differential diffusion. For example, the semi-porous membrane may be dialysis tubing, a dialyzer, a bioreactor, or other similar structure. In embodiments, the pores of the semi-porous membrane can be sized to permit passage of nutrients and any waste products present in the nutrient media solution 112, but block passage of any growth factors or hormones produced by the biological cell culture (e.g., molecules beneficial to the biological cell culture) present in the aqueous solution returned to the filtering unit 115 from the culture container 105 along fluid path 140-A. Thus, these beneficial molecules may be retained within the closed-loop perfusion system 100 for the benefit of the biological cell culture in culture container 105 while some beneficial molecules may enter the system and harmful molecules may exit the system via the semi-porous membrane. The operation of the filtering unit 115 and media reservoir 110 is described in further detail below with respect to FIG. 2A. In some implementations, the media reservoir 110 may additionally be connected to a secondary reservoir that provides fresh nutrient media solution as described in further detail below with respect to FIG. 2B.

As shown, the closed-loop perfusion system 100 connects culture container 105 and filtering unit 115 via fluid paths 140-A and 140B. In embodiments, fluid paths 140-A, 140-B may be spans of tubing that include one-way valves to control the flow direction of media circulated within the fluid paths. Fluid path 140-A connects the output (e.g., an output valve or connector) of the culture container 105 to the input (e.g., an input valve or connector) of filtering unit 115. Similarly, fluid path 140-B connects the output (e.g., an output valve or connector) of the filtering unit 115 to the input (e.g., an input valve or connector) of culture container 105. As shown in FIG. 1, the arrows of fluid path 140-A and 140-B illustrate that the flow of media within the fluid paths proceed in a single direction. Note, that while the fluid paths 140-A and 140-B as illustrated in FIG. 1 depict the flow of media in a clockwise direction, in other embodiments the closed-loop perfusion system 100 may be configured such that the flow of media may proceed in a counterclockwise direction.

The closed-loop perfusion system 100 may also include a pump 120 to circulate the media within fluid paths of the system. In some embodiments, pump 120 can initially deliver the nutrient media solution 112 through fluid path 140-B to culture container 105 in order to feed the biological cell culture contained within culture container 105. The pumping action of pump 120 can thus cause the nutrient media solution 112 to be mixed with any beneficial molecules produced by the biological cell culture within culture container 105 and exit the culture container 105 to return to the filtering unit 115 via fluid path 140-A. In subsequent circulatory cycles within the system, pump 120 can deliver the mixture of the nutrient media solution 112 and any beneficial molecules that are produced by the contents of the sealed biological cell culture container 105 through fluid path 140-B to return to culture container 105.

In some implementations, pump 120 may be a pump that maintains an approximately consistent flow rate of the media within the closed-loop perfusion system 100. In an illustrative example, pump 120 may maintain a flow rate of 1 milliliter per hour (1 ml/hour) to provide 1 circulatory pass of the media solution within the system in 24 hours. Other flow rates may also be used. In embodiments, pump 120 may be a peristaltic pump, a piezo pump, or other similar device. Thus, the media solution is fed to the biological cell culture in culture container 105 at the same rate as media is extracted from culture container 105. As such, the culture container 105 can consistently remain full of nutrient media solution while being presented with a fresh batch of the nutrient media solution at all times. At the same time, beneficial molecules produced by the cell culture may be retained within the system and recirculated back to the culture container. It should be noted, that while FIG. 1 depicts pump 120 in a particular location within fluid path 140-A, in some implementations, pump 120 may be in another location within fluid path 140-A, or may be located within fluid path 140-B.

As noted above, in various embodiments, closed-loop perfusion system 100 may include additional components that are coupled to fluid paths 140-A and 140-B. In some implementations, closed-loop perfusion system 100 may include one or more sensors 125 (coupled to fluid path 140-B) and/or 126 (coupled to fluid path 140-A) to measure chemical contents of the media within the respective fluid paths. For example, sensor 125 may measure the chemical contents of the nutrient media solution that exits the filtering unit prior to entering the culture container. Similarly, sensor 125 may measure the contents of the mixture of the nutrient media solution and the beneficial molecules produced by the biological cell culture as the mixture exits culture container 105. In various embodiments, the sensors 125, 126 may be used to measure pH level, carbon dioxide ($CO_2$) content level, oxygen ($O_2$) content level, a nutrient level, or the like.

In embodiments, the sensors 125, 126 may be independently powered and configured to provide alerts and/or signals if the measured contents of the media fall outside predefined thresholds or threshold ranges. For example, if the pH of the media rises above a high threshold level which may be damaging to the biological cell culture, the sensors can trigger a visible or audible notification that the media may need to be refreshed. Alternatively, the sensors 125, 126 may be controlled and/or monitored by computing device 150 via network 160 as described below.

In some implementations, sensor 125 or 126 may be a temperature sensor. The temperature sensor can be used to measure the temperature of at least one of the nutrient media solution 112, the output of the sealed biological cell culture container 105, or the mixture of the nutrient media solution and the filtered output of the sealed biological cell culture container 105 within the fluid paths 140-A, 140-B of closed-loop perfusion system 100. If the temperature sensor detects that the temperature of the media is outside a temperature range, an instruction can be sent to heating/cooling element 130 to either heat or cool the media as appropriate.

For example, assuming a predefined temperature range between 36.5 degrees Celsius and 37.5 degrees Celsius, should the temperature sensor detect that the temperature of the media falls below 36.5 degrees Celsius, heating/cooling element 130 can be engaged to heat the media until the temperature rises to be within the temperature range. Similarly, if the temperature rises above 37.5 degrees Celsius, heating/cooling element 130 can be engaged to cool the media until the temperature falls to be within the temperature range. In some implementations, the heating/cooling element 130 can be connected to and controlled by the temperature sensor 125, 126 independently of any other sensors within the system. Alternatively, the temperature sensor 125, 126 and heating/cooling element 130 may be connected to and controlled by perfusion system controller 155 of computing device 150.

In some implementations, closed-loop perfusion system 100 may include an access port 135 that can allow access to the contents of the fluid paths for extraction from and addition to the media solution within the system. It should be noted that although a single access port 135 is depicted in FIG. 1, in other embodiments multiple access ports 135 can be positioned in different locations within the fluid paths 140-A and 140-B. For example, in one embodiment, access port 135 may be coupled to fluid path 140-B to allow the addition of one or more compounds into the system. As a result, the added compound(s) may be circulated into the culture chamber 105 and subsequently into fluid path 140-A to return to the filtering unit 115. In various implementations, the added compound(s) can include nutrient compounds, pharmaceutical compounds, chemical reward stimulus compounds (e.g., dopamine), or other similar chemical compound that may be measured and/or tested within the closed-loop perfusion system.

In some implementations, access port 135 can be coupled to fluid path 140-A to allow a sample of the output of the sealed biological culture container 105 to be extracted from the closed-loop perfusion system 100. In such implementations, an additional media sampling device (not pictured) may be attached to the access port to extract a sample of the media within fluid path 140-A. In this manner, the contents of the media in fluid path 140-A may be analyzed outside the closed-loop system to determine if there are any differences between the chemical composition of the media within fluid path 140-A as compared to the chemical composition of the media within fluid path 140-B.

In some implementations, the closed-loop perfusion system 100 may also include one or more computing devices 150 connected to one or more of the components described above via a network 160 or directly. The network 160 may be a local area network, a wide area network, a private network (e.g., an intranet), a public network (e.g., the Internet), or a combination thereof.

The computing devices 150 may include physical machines and/or virtual machines hosted by physical machines. The physical machines may be rackmount servers, desktop computers, or other computing devices. In one embodiment, the computing devices 150 include virtual machines managed and provided by a cloud provider system. Each virtual machine offered by a cloud service provider may be hosted on a physical machine configured as part of a cloud. Such physical machines are often located in a data center. The cloud provider system and cloud may be provided as an infrastructure as a service (IaaS) layer. One example of such a cloud is Amazon's® Elastic Compute Cloud (EC2®).

The computing devices 150 may host a perfusion system controller 155 that can control and/or manage the various components of the closed-loop perfusion system 100 described above. The perfusion system controller 155 may be hosted on one computing device 150 that manages all components within closed-loop perfusion system 100. Alternatively, perfusion system controller 155 may be replicated and hosted on separate computing devices 150 that are connected via network 160, where each controls a particular component of the system. For example, the flow control operations of pump 120 may be controlled by one computing device 150, while the operations of sensors 125 and 126 may be controlled by a separate computing device 150.

Perfusion system controller 155 may manage the flow control operations of pump 120 by sending instructions to the pump 120 that indicated a desired flow rate to be maintained. Additionally, perfusion system controller 155 may receive notifications from sensors 125, 126, or the pump 120 itself that indicate the actual flow rate of the nutrient media solution through the closed-loop system 100 and send updated instructions to pump 120 to modify the flow rate accordingly to match the desired flow rate.

Additionally, perfusion system controller 155 may receive notifications/signals from any of the sensors 125, 126 that measure the chemical contents of the nutrient media solution at various points throughout the closed-loop system 100. For example, sensor 125 may be located on fluid path 140-B prior to an input port of culture container 105 and sensor 126 may be located on fluid path 140-A after an exit port of culture container 105. Perfusion system controller 155 may receive notifications from each sensor as to the chemical contents of the nutrient media solution and report any deviation between the two measurements by sending an alert message to an interested party (e.g., an email, text message, etc.), generate an audible alert, or send a notification to a master console of the computing device 150. Similarly, perfusion system controller 155 may perform similar notifications if any single sensor reports a measurement that is outside a predetermined threshold without comparing it to measurement of another sensor. For example, if perfusion system controller receives a notification from sensor 125 with a pH level of the nutrient media solution within fluid path 140-B, it can then determine if the measurement falls outside of an acceptable pH range (e.g., the measured value meets or exceeds a high threshold value for pH, or falls below a low threshold value for pH). If so, the perfusion system controller 155 can send an alert as described above. Additionally, in some implementations, the perfusion system controller can send an instruction to a chemical delivery device that is connected to an access port 135 to inject one or more compounds into the nutrient media solution until the measured pH returns to a value within the acceptable pH range.

Perfusion system controller 155 may manage the operations of temperature sensors 125, 126 and control the actions of heating/cooling element 130 responsive to the measurements of the temperature sensors 125, 126 as described above. For example, perfusion system controller 155 may send an instruction to temperature sensor 125, 126 to measure at least one of the nutrient media solution, the output of the sealed biological cell culture container 105, or the mixture of the nutrient media solution and the filtered output of the sealed biological cell culture container 105. Responsive to detecting that the temperature falls below the low temperature threshold of a temperature range, perfusion system controller 155 may send a signal to heating/cooling element 130 to heat at least one of the nutrient media solution, the output of the sealed biological cell culture container 105 or the mixture of the nutrient media solution and the filtered output of the sealed biological cell culture container 105 until the temperature is within the temperature range. Similarly, responsive to detecting that the temperature exceeds a high temperature threshold of the temperature range, perfusion system controller 155 may send a signal to heating/cooling element 130 to cool at least one of the nutrient media solution, the output of the sealed biological cell culture container or the mixture of the nutrient media solution and the filtered output of the sealed biological cell culture container until the temperature is within the temperature range.

In some implementations, culture container 105 can include a multielectrode array (MEA) 170 or other neural processing unit. An MEA 170 is a device that contains multiple plates or shanks through which neural signals are obtained and/or delivered. The plates or shanks are generally arranged in a grid or other array and serve as a neural interface that connects neurons to electronic circuitry. The MEA 170 can include cultured biological neurons (e.g., cultured from stem cells) and/or extracted neurons (e.g., extracted from a rat brain). In some implementations, the MEA 170 can include other types of cultured biological cells/tissues that can be stimulated electronically, such as muscle cells. The MEA 170 can be used to perform electrophysiological experiments on dissociated cell cultures (e.g., cultures of biological neurons). With dissociated neuronal cultures, the neurons spontaneously form biological neural networks.

Biological neurons create ion currents through their membranes when excited, causing a change in voltage between the inside and the outside of the cell. When recording, the electrodes on an MEA 170 transduce the change in voltage from the environment carried by ions into currents carried by electrons (electronic currents). When stimulating, electrodes may transduce electronic currents into ionic currents through the media. This triggers the voltage-gated ion channels on the membranes of the excitable neurons, causing the neuron to depolarize and trigger an action potential.

In various embodiments, the MEA 170 can include the biological neurons disposed on the MEA 170 and one or more sensors 175 to measure the electrical signals output by the biological neurons. In some implementations, the MEA 170 can be additionally coupled to computing device 150

(either directly or through network 160) such that perfusion system controller 155 can receive digital signals from the MEA 170 that indicates that the biological neurons have entered a reward stimulus condition, and send an instruction to a chemical delivery device to provide a chemical reward stimulus to the contents of the sealed biological culture container for the biological neurons in the MEA 170. For example, perfusion system controller 155 can send an instruction to a chemical delivery device coupled to access port access port 135 of fluid path 140-B to provide an injection of dopamine to the system for delivery to the MEA 170.

Figure 2A:
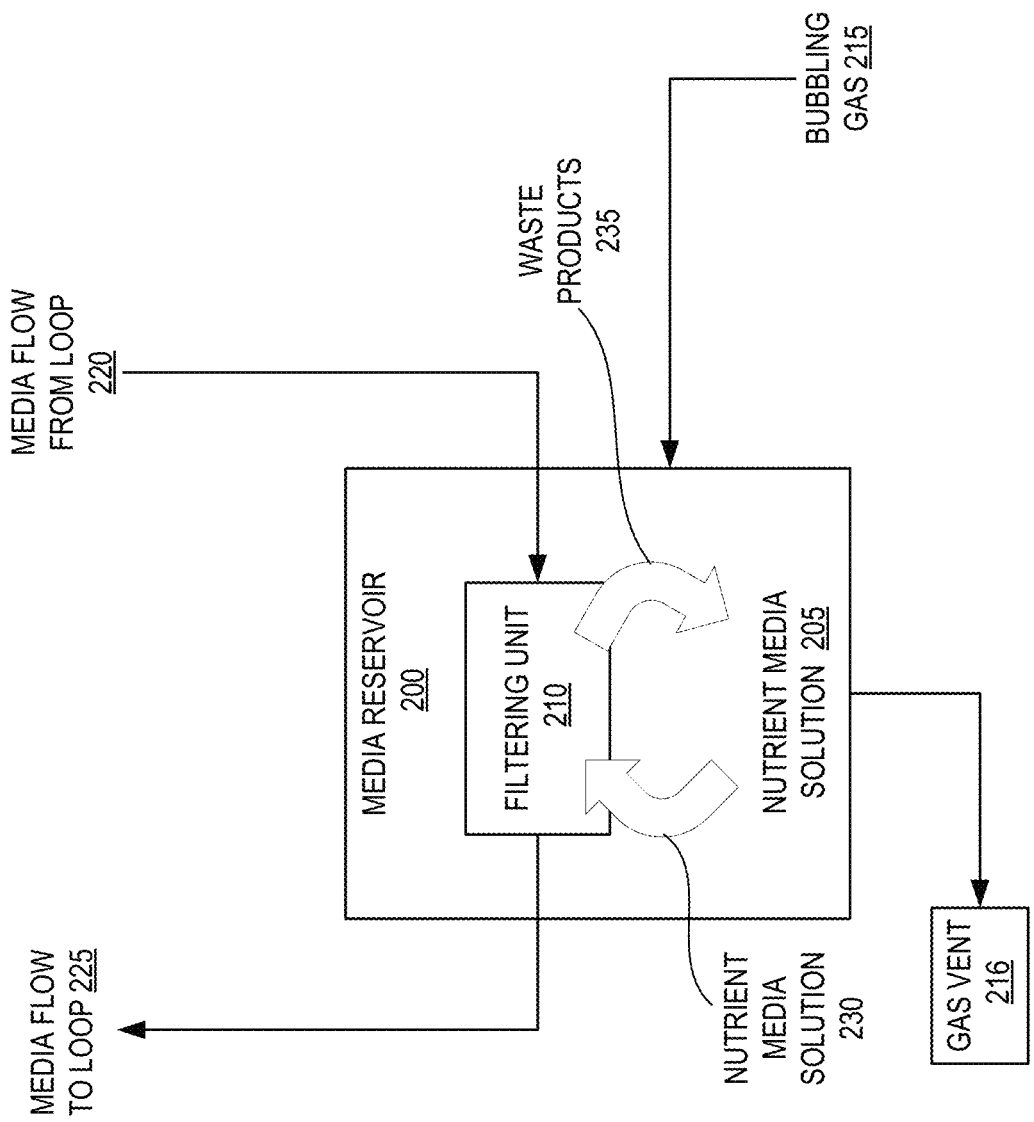
FIG. 2A illustrates a filtering unit with a single media reservoir for a closed-loop perfusion system, in accordance with one embodiment.

FIG. 2A illustrates a filtering unit with a single media reservoir 200 for a closed-loop perfusion system, in accordance with one embodiment. As shown, media reservoir 200 includes a nutrient media solution 230 as well as a filtering unit 210 disposed within the media reservoir 200. In some implementations, media reservoir 200 and filtering unit 210 correspond to media reservoir 110 and filtering unit 115 of FIG. 1 respectively.

As noted above, nutrient media solution 230 is circulated through the closed-loop perfusion system to feed the biological cells in the culture container. The nutrient media solution 230 can include trophic growth hormone factor for the biological culture (e.g., neurotrophins, ciliary neurotrophic factors (CNTF), glial cell line derived neurotrophic factors (GDNF), ephrins, epidermal growth factors (EGF), transforming growth factors (TGF), or neuron derived neurotrophic factors (NDNF)), a basal media (e.g., an inorganic salt, an amino acid, an energetic substrate, a vitamin, a pH buffer, or a pH indicator), and/or a supplement (e.g., a vitamin, a protein, a hormone steroid, a hormone thyroid, an essential fatty acid, a lipid, a sulfate mineral, an organic chemical compound, a monosaccharide, or a nucleotide).

As shown, media flow from loop 220 represents the flow of nutrient media solution from the sealed biological culture container through the filtering unit 210 in the media reservoir 200 (e.g., via fluid path 140-A of FIG. 1). This can include the nutrient media solution 230 from media reservoir 200 as well as any beneficial molecules and/or metabolic waste products (e.g., lactic acid/lactate, ammonia, or any similar product that can negatively impact the biological cell culture) generated by the biological cell culture. Media flow to loop 225 represents the flow of nutrient media solution from the filtering unit 210 back through the loop into the sealed biological culture container (e.g., via fluid path 140-B of FIG. 1).

In some implementations, the walls of the filtering unit 210 may be made up of semi-porous membrane sized to permit some molecules (e.g., nutrients, waste) to exit the closed-loop system while retaining other molecules (e.g., beneficial molecules). In an illustrative example, the pores may be sized to allow molecules larger than 5 kilodaltons (5 kDa) to be retained within the closed-loop and to allow molecules smaller than 5 kDa to diffuse into and/or out of the closed-loop circuit. Alternatively, the pores may be sized to retain molecules with different molecular weights. As the media flow from loop 220 enters the filtering unit 210, the pores of the semi-porous membrane of filtering unit permit passage (diffusion out of the loop) of the waste products 235 into the media reservoir for collection and/or disposal. Additionally, the semi-porous membrane permits passage of nutrient media solution 230 stored within media reservoir 200 into the loop (depicted by the flow of nutrient media solution 230 into filtering unit 210). Further, the pores of the semi-porous membrane are sized to block the passage (e.g., retain within the loop) of any beneficial molecules from output of the sealed biological cell culture container. In other words, any beneficial molecules such as growth factor or hormones produced by the biological culture are prevented from exiting the loop and are, therefore, retained within the loop. As noted above, the semi-porous membrane of the filtering unit may be composed of dialysis tubing.

Bubbling gas can be injected into media reservoir 200 to assist with regulating the gas composition within the media reservoir 200, and subsequently into the media flow to loop 225, for optimal cellular growth. In such instances, a gas vent 216 can also be connected to media reservoir 200 to allow gas to escape the reservoir and maintain a stable pressure.

Figure 2B:
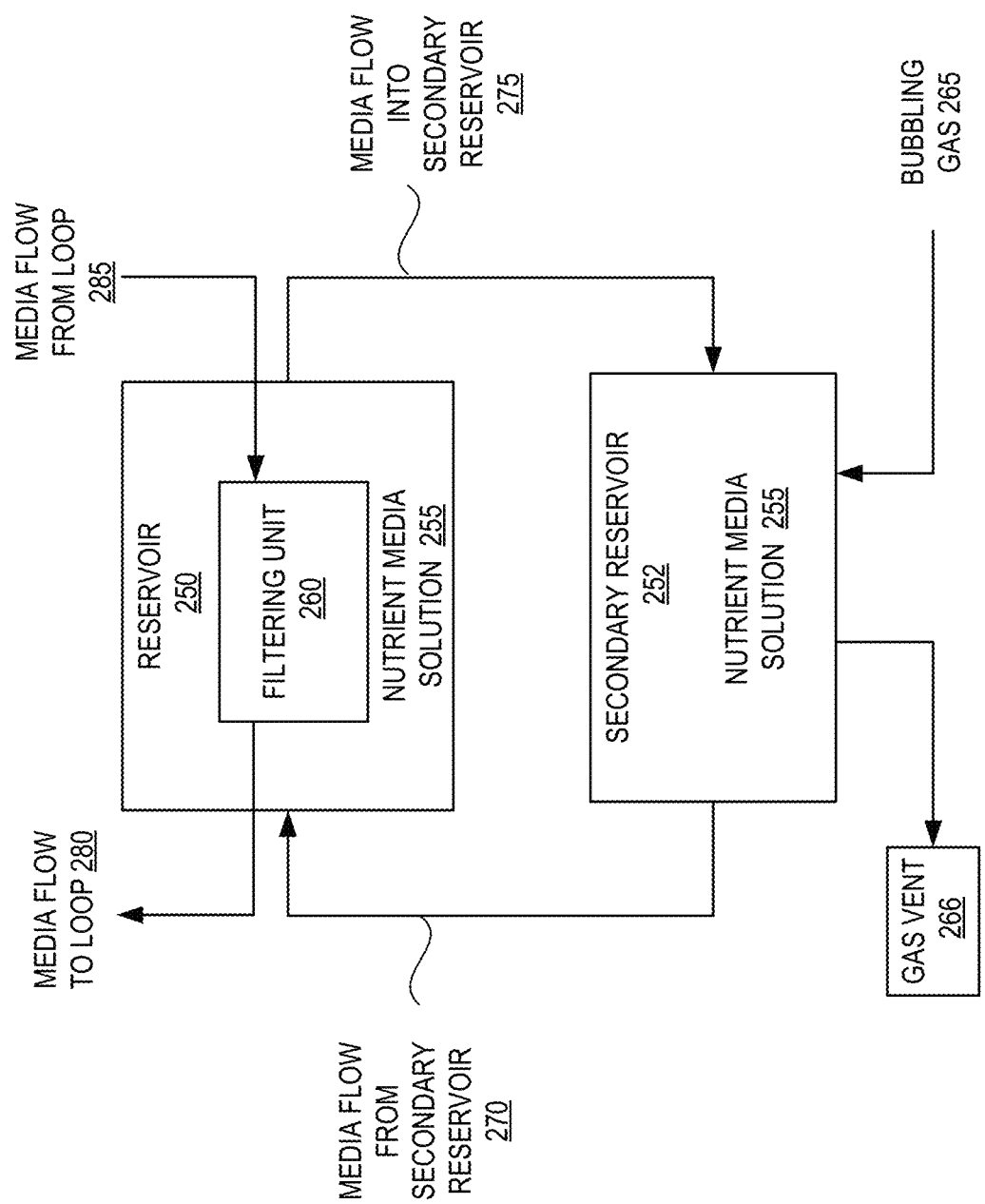
FIG. 2B illustrates a filtering unit with primary and secondary media reservoirs for a closed-loop perfusion system, in accordance with one embodiment.

FIG. 2B illustrates a filtering unit with primary and secondary media reservoirs for a closed-loop perfusion system, in accordance with one embodiment. As shown, media reservoir 250 includes a nutrient media solution 255 as well as a filtering unit 260 disposed within the media reservoir 250. In some implementations, media reservoir 250 corresponds to media reservoir 110 of FIG. 1 and/or media reservoir 200 of FIG. 2A. Similarly, filtering unit 260 may correspond to filtering unit 115 of FIG. 1 and/or filtering unit 210 of FIG. 2A. FIG. 2B also depicts a secondary reservoir 252 that contains additional nutrient media solution 255 that can be transferred into the primary reservoir 250 for use within the closed-loop system. The secondary reservoir 252 can thus facilitate an alternative method of refreshing the nutrient media solution within the closed-loop system that reduces any possible disruption to the primary reservoir and filtering unit.

Similar to FIG. 2A, media flow from loop 285 represents the flow of nutrient media solution from the sealed biological culture container through the filtering unit 260 in the media reservoir 250 (e.g., via fluid path 140-A of FIG. 1). Media flow to loop 280 represents the flow of nutrient media solution from the filtering unit 260 back through the loop into the sealed biological culture container (e.g., via fluid path 140-B of FIG. 1).

As shown, a secondary reservoir 252 may be connected to reservoir 250 by secondary fluid paths made up of additional spans of tubing and one-way valves to control the direction of media flow between the two chambers. Media flow from secondary reservoir 270 represents the flow of nutrient media solution 255 from the secondary reservoir 250 into reservoir 250. Similarly, media flow into secondary reservoir 275 represents the flow of nutrient media solution 255 from reservoir 250 back to the secondary reservoir 252. In some implementations, the flow of nutrient media solution 255 between reservoir 250 and secondary reservoir 252 may be controlled by a fluid exchange system that exchanges the fluid contents of the secondary reservoir 252 and the reservoir 250 via the secondary fluid paths. In an illustrative example, the fluid exchange system injects bubbling gas 265 into the secondary reservoir 252 to regulate the gas composition within the secondary reservoir 252, and subsequently into the reservoir 255 and the media flow to loop 280, for optimal cellular growth. In such cases, a gas vent 266 may be connected to the secondary reservoir 252 to allow some gas to escape and to maintain a stable gas pressure within the reservoir. Alternatively, a secondary pump (not pictured) may be connected to one of the secondary fluid paths to control the flow of nutrient media solution 255 between the two reservoirs.

Figure 2C:
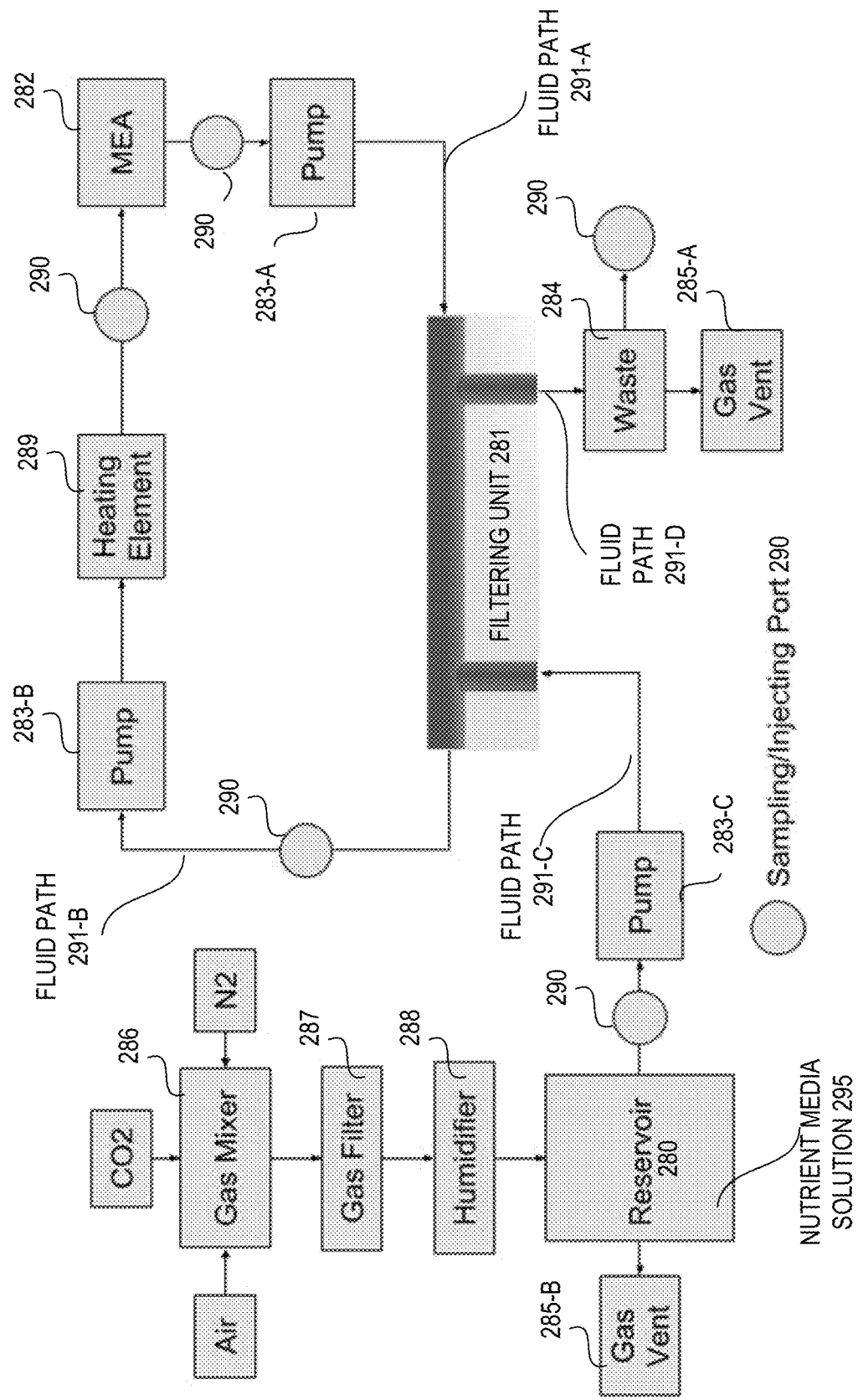
FIG. 2C illustrates a filtering unit that is externally attached to a single media reservoir for a closed-loop perfusion system, in accordance with one embodiment.

FIG. 2C illustrates a filtering unit that is externally attached to a single media reservoir for a closed-loop perfusion system, in accordance with one embodiment. As shown, filtering unit 281 is connected to multielectrode array (MEA) 282 (e.g., a biological cell culture container) by fluid paths 291-A and 291-B. In some implementations, filtering unit 281 corresponds to filtering unit 115 of FIG. 1. Similarly, MEA 282, fluid path 291-A, and fluid path 291-B may correspond to culture container 105, fluid path 140-A, and fluid path 140-B of FIG. 1, respectively. In some implementations, MEA 282 may be replaced with another type of cell culture container that does not include a multi-electrode array.

As described above with respect to FIG. 1, one or more pumps (e.g., pumps 283-A, 283-B) can be coupled to fluid paths 291-A and 291-B to circulate nutrient media solution between filtering unit 281 and MEA 282. Additionally, heating element 289 may be coupled to fluid path 291-B to regulate the temperature of the circulating media flow prior to reaching MEA 282. Also as described above, sampling/injecting ports 290 may be coupled to fluid paths 291-A, 291-B to provide access to the nutrient media solution within the system to extract samples of the media within the loop or inject additional components into the solution within the loop. In some implementations, sampling/injecting ports 290 may correspond to access port 135 of FIG. 1.

As shown, filtering unit 281 may be connected, by a third fluid path (e.g., fluid path 291-C), to media reservoir 280 that includes a nutrient media solution 295. In some implementations, media reservoir 280 corresponds to media reservoir 110 of FIG. 1. In embodiments, reservoir 280 may be connected to a fluid exchange system (e.g., a pump 283-C) that provides the nutrient media solution 295 within the reservoir to filtering unit 281 via fluid path 291-C. In some implementations, reservoir 280 may be additionally connected to one or more elements that can regulate gas levels within reservoir 280. For example, gas mixer 286 may receive Air, carbon dioxide ($CO_2$) and Nitrogen ($N_2$), and create a gas mixture to provide to gas filter 287. Gas filter 287 can filter the mixture received from gas mixer 286 to remove impurities or to sterilize the gas before entering media reservoir 280, and to provide the resulting gas mixture to humidifier 288. Humidifier 288 may then add moisture to the gas mixture to regulate the humidity levels of the nutrient media solution 295 within the reservoir 280. In some implementations, reservoir 280 may also be connected to a gas vent 285-B that can allow any excess gas to escape and to maintain a stable gas pressure within the media reservoir 280.

As shown, filtering unit 281 may also be connected to a waste reservoir 284 by a fourth fluid path (e.g., fluid path 291-D). Waste reservoir 284 can collect any metabolic waste molecules produced by the MEA and filtered out of the circulating media solution within the closed-loop by filtering unit 281 as described above. In some implementations, waste reservoir 284 may also be connected to a gas vent 285-A to allow excess gas to escape and to maintain a stable gas pressure within waste reservoir 284.

Pump 283-C may pump fresh nutrient media solution from reservoir 280 into filtering unit 281. The fresh nutrient media solution may pass freely through a semi-permeable membrane of the filtering unit 281. Pump 283-C and/or pump 283-A may further force an output of MEA 282 through the semi-permeable membrane into waste reservoir 284. The semi-permeable membrane may have pores that are sized to permit the passage (e.g., via diffusion) of waste products in the output from MEA 282, but that are small enough to block passage of beneficial molecules. Accordingly, the beneficial molecules may be maintained within the closed-loop circuit.

In some implementations, sampling/injecting ports 290 may be coupled to fluid paths 291-C, 291-D to provide access to the nutrient media solution within the system to extract samples of the media within the loop or inject additional components into the solution within the loop. In some implementations, sampling/injecting ports 290 may correspond to access port 135 of FIG. 1.

Figure 3A:
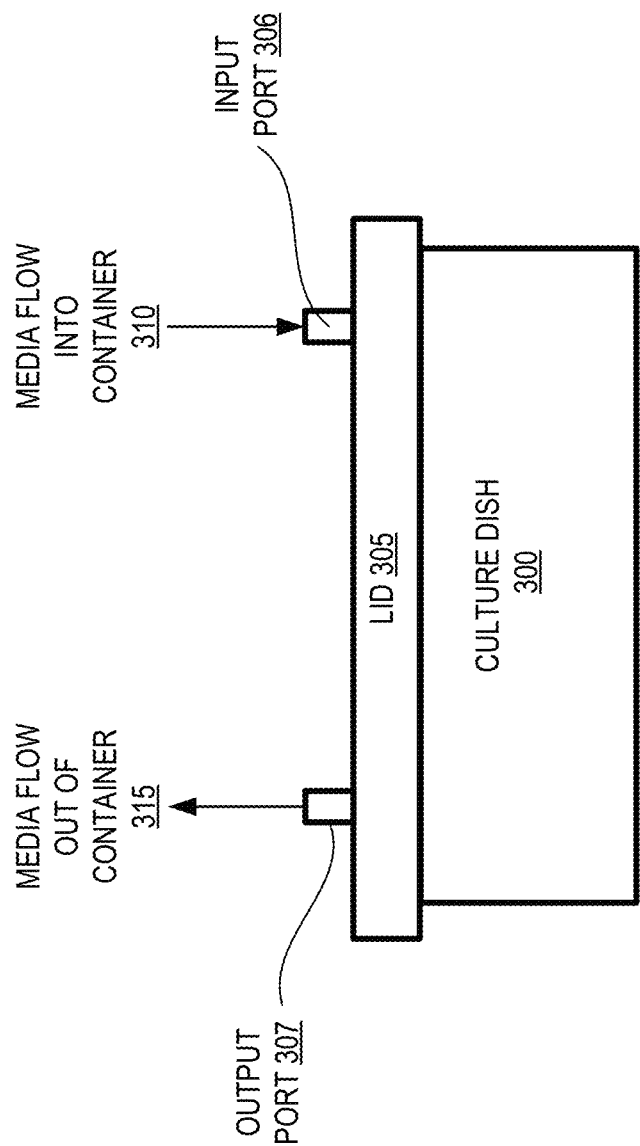
FIG. 3A illustrates one embodiment of a flat lid for a culture dish, in accordance with one embodiment.

FIG. 3A illustrates one embodiment of a flat lid 305 for a culture dish 300, in accordance with one embodiment. In some implementations, the flat lid 305 and culture dish 300, when combined, can correspond to the sealed biological culture container 105 of FIG. 1. As shown, lid 305 can include an input port 306 and an output port 307. In some implementations, the input port 306 can be connected to the fluid path of the closed-loop perfusion system that transfers nutrient media solution from the filtering unit into the culture container (e.g., fluid path 140-B of FIG. 1). This path is illustrated by media flow into container 310. Similarly, the output port 307 can be connected to the fluid path of the closed-loop perfusion system that transfers nutrient media solution from the culture container into the filtering unit (e.g., fluid path 140-A of FIG. 1). This path is illustrated by media flow out of container 315.

In embodiments, lid 305 can be connected to culture dish 300 using an O-ring type gasket to provide a water tight seal. In some implementations, lid 305 may be transparent to allow imaging of the contents of the culture dish 300. In some implementations, lid 305 may be composed of medical grade materials such as polystyrene, a United States Pharmacopeia (USP) Class VI Plastic, glass, or the like.

FIGS. 3B-3C illustrate views of an alternate embodiment of a flat lid for a culture container, in accordance with one embodiment. Top view 320 for FIG. 3B illustrates the top side of a flat lid for the culture container. As shown, top view 320 depicts input port 321 and output port 322. In some implementations, the input port 321 can be connected to the fluid path of the closed-loop perfusion system that transfers nutrient media solution from the filtering unit into the culture container (e.g., fluid path 140-B of FIG. 1). This path is illustrated by media flow into container 335. Similarly, the output port 322 can be connected to the fluid path of the closed-loop perfusion system that transfers nutrient media solution from the culture container into the filtering unit (e.g., fluid path 140-A of FIG. 1). This path is illustrated by media flow out of container 330.

Bottom view 325 of FIG. 3C depicts the underside of the lid with input port opening 327 that allows nutrient media solution into the container (e.g., illustrated by media flow into container 345) and output port opening 326 that allows nutrient media solution to exit the container (e.g., illustrated by media flow media flow out of container 340).

Figure 3D:
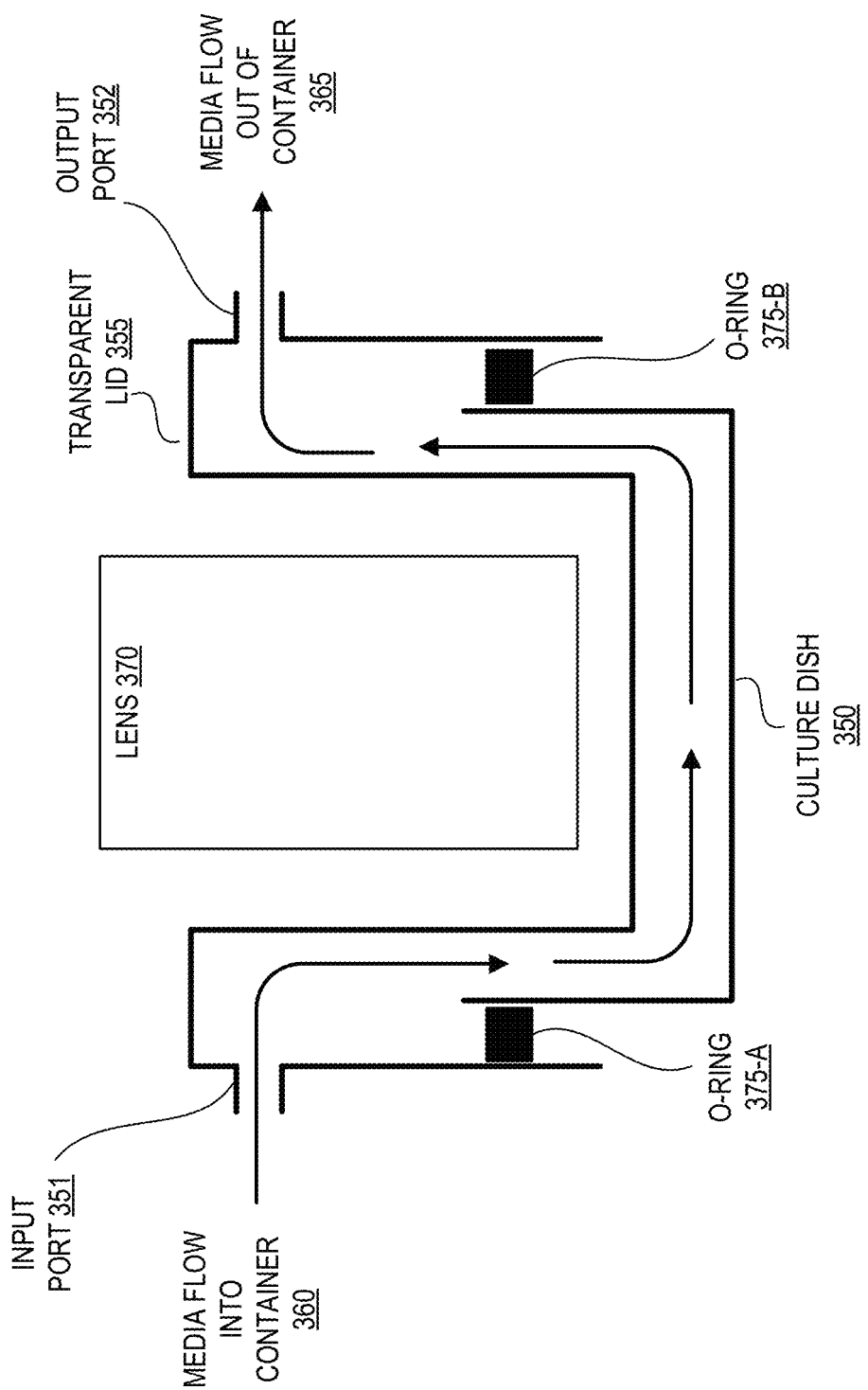
FIG. 3D illustrates an embodiment of a transparent lid for a culture dish, in accordance with one embodiment.

FIG. 3D illustrates an embodiment of a transparent lid 355 for a biological culture dish 350, in accordance with one embodiment. In some implementations, the transparent lid 355 and culture dish 350, when combined, can correspond to the sealed biological culture container 105 of FIG. 1. As shown, transparent lid 355 can include an input port 351 and an output port 352. In some implementations, the input port 351 can be connected to the fluid path of the closed-loop perfusion system that transfers nutrient media solution from the filtering unit into the culture container (e.g., fluid path 140-B of FIG. 1). This path is illustrated by media flow into container 360. Similarly, the output port 352 can be connected to the fluid path of the closed-loop perfusion system that transfers nutrient media solution from the culture container into the filtering unit (e.g., fluid path 140-A of FIG. 1). This path is illustrated by media flow out of container 365.

In embodiments, transparent lid 355 can be coupled to the biological culture dish 350 with a water-tight seal. In some implementations, the water-tight seal provided using one or more O-ring type gaskets (e.g., O-ring 375-A, 375-B). Transparent lid 355 may include a concave portion that is a threshold distance from the contents of the biological culture dish 350 and that is configured to receive a camera component (e.g., lens 370) to enable the image capture of the contents of the biological culture dish 350. In an illustrative example, the concave portion of transparent lid 355 may have a thickness of not more than 1.14 mm.

Figure 4:
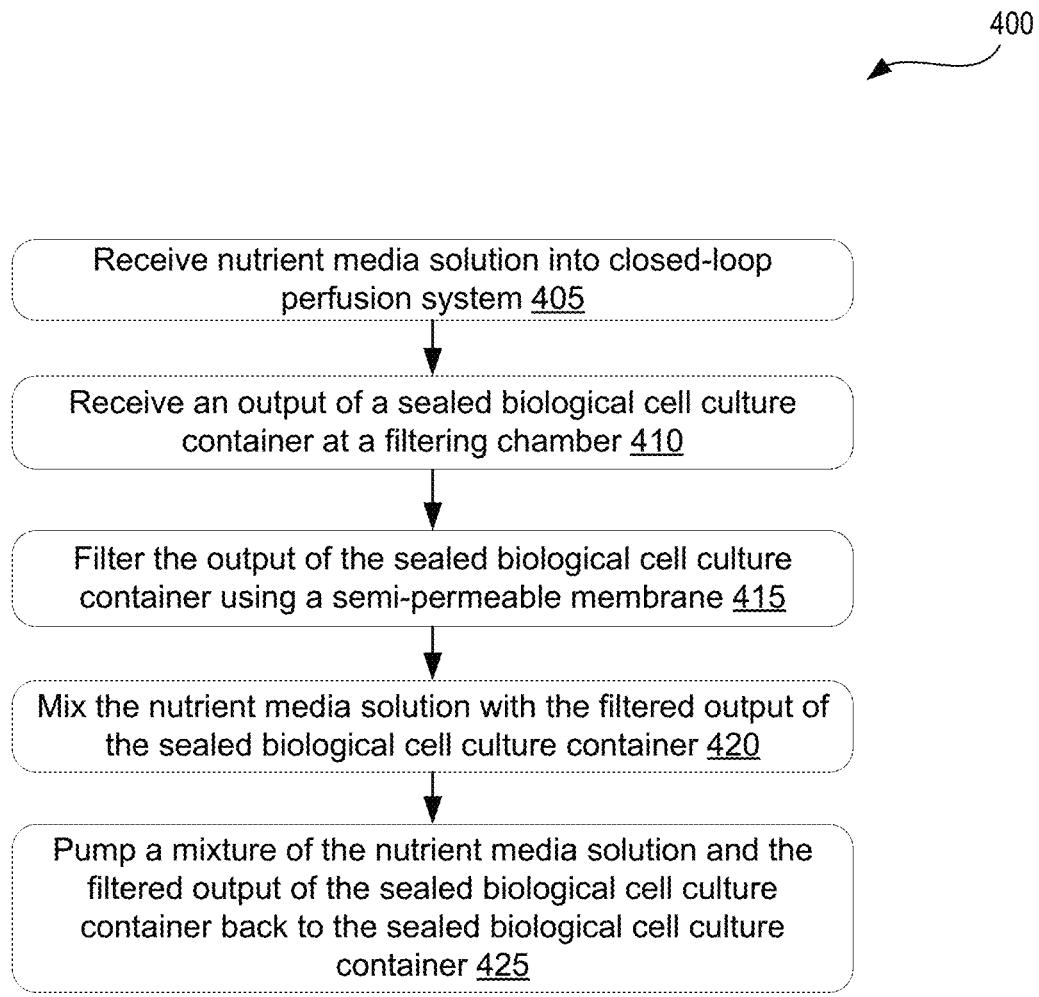
FIG. 4 is a flow diagram illustrating one embodiment for a method of controlling a closed-loop perfusion system.

FIG. 4 is a flow diagram illustrating one embodiment for a method 400 of controlling a closed-loop perfusion system. The method may be performed by components of a closed-loop perfusion system and/or processing logic of a perfusion system controller of a computing device, which may include hardware (e.g., circuitry, dedicated logic, programmable logic, microcode, etc.), software (such as instructions run on a processing device, a general purpose computer system, or a dedicated machine), firmware, or a combination thereof. In an illustrative example, the method may be performed by perfusion system controller 155 of computing device 150 in FIG. 1.

For simplicity of explanation, the method is depicted and described as a series of acts. However, acts in accordance with this disclosure can occur in various orders and/or concurrently and with other acts not presented and described herein. Furthermore, not all illustrated acts may be performed to implement the method in accordance with the disclosed subject matter. In addition, those skilled in the art will understand and appreciate that the method could alternatively be represented as a series of interrelated states via a state diagram or events.

At block 405, the closed-loop perfusion system receives a nutrient media solution into the closed-loop perfusion system. In some implementations, the closed-loop perfusion system includes a sealed biological cell culture container, a filtering unit, a first fluid path between the sealed biological cell culture container and the filtering unit, and a second fluid path between the sealed biological cell culture container and the filtering unit. In some implementations, the nutrient media solution is received through a semi-permeable membrane of the filtering unit. In some implementations, the closed-loop system also includes multiple one-way valves to control the direction of flow of the output of the sealed biological cell culture container and the mixture of the nutrient media solution and the filtered output of the sealed biological cell culture container using the plurality of one-way valves.

At block 410, the closed-loop perfusion system receives an output of the sealed biological cell culture container at the filtering unit via the first fluid path, where the output includes beneficial molecules produced by a biological cell culture in the sealed biological cell culture container and waste products from the biological cell culture. In some implementations, the beneficial molecules include at least one of a growth factor or a hormone produced by the biological cell culture. In some implementations, the waste products include metabolic waste such as lactic acid/lactate or ammonia. In some implementations, the waste products leave the filtering unit via the semi-porous membrane, and wherein the nutrient media solution enters the filtering unit via the semi-porous membrane, via a diffusion process and/or an osmosis process.

At block 415, the closed-loop perfusion system filters the output of the sealed biological cell culture container using the semi-permeable membrane to retain the beneficial molecules within the closed-loop system while removing the waste products. At block 420, the closed-loop perfusion system mixes the nutrient media solution with the filtered output of the sealed biological cell culture container. At block 425, the closed-loop perfusion system pumps a mixture of the nutrient media solution and the filtered output of the sealed biological cell culture container back to the sealed biological cell culture container through the second fluid path.

Figure 5:
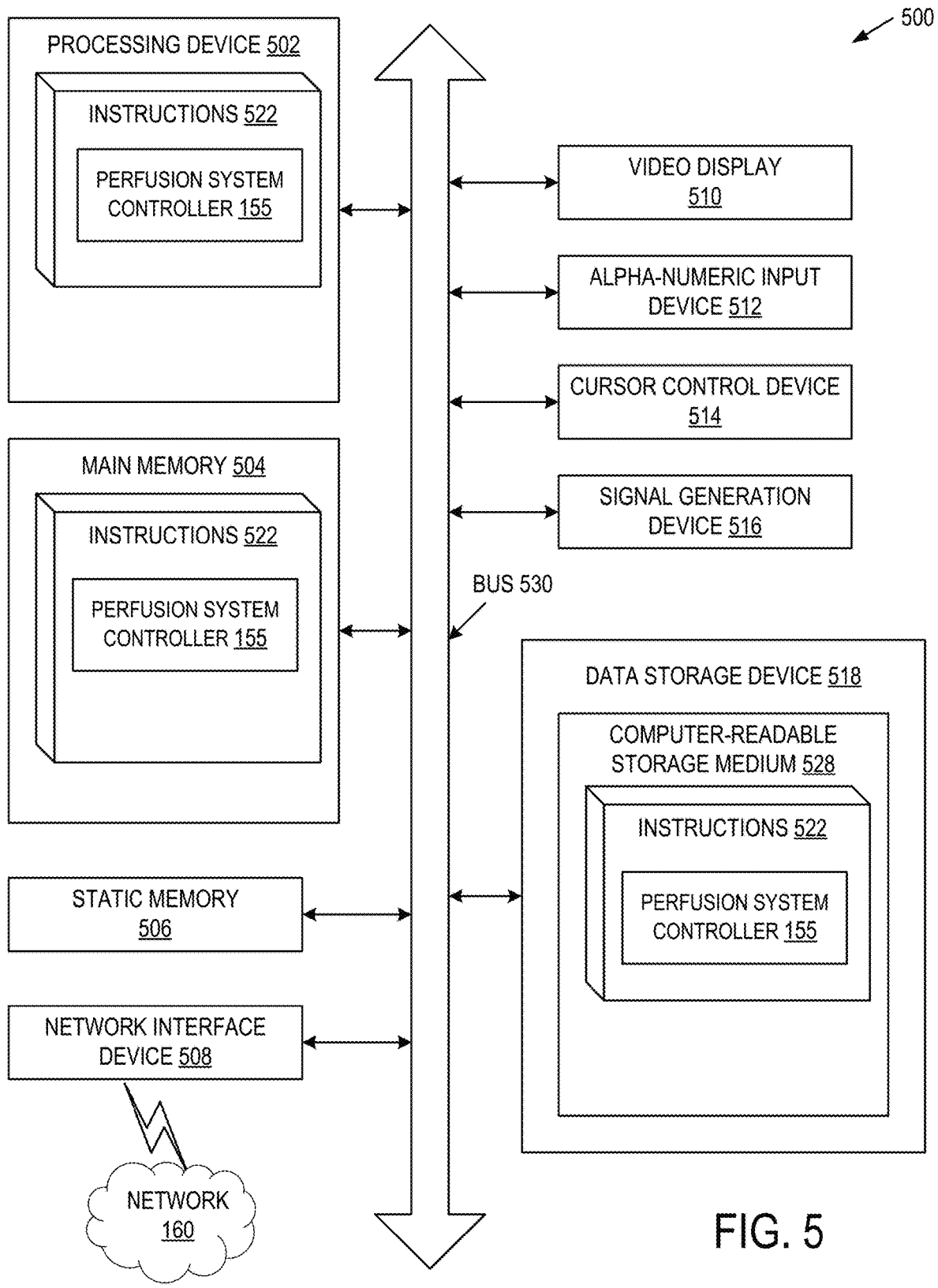
FIG. 5 illustrates an example computing device, in accordance with one embodiment.

FIG. 5 illustrates a diagrammatic representation of a machine in the example form of a computing device 500 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 500 includes a processing device 502, a main memory 504 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a secondary memory (e.g., a data storage device 518), which communicate with each other via a bus 530.

Processing device 502 represents one or more general-purpose processors such as a microprocessor, central processing unit, or the like. More particularly, the processing device 502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. Processing device 502 is configured to execute the processing logic (instructions 522) for performing the operations and steps discussed herein.

The computing device 500 may further include a network interface device 508. The computing device 500 also may include a video display 510 (e.g., a liquid crystal display (LCD) or a cathode ray tube (CRT)), an alphanumeric input device 512 (e.g., a keyboard), a cursor control device 514 (e.g., a mouse), and/or a signal generation device 516 (e.g., a speaker).

The data storage device 518 may include a machine-readable storage medium (or more specifically a computer-readable storage medium) 528 on which is stored one or more sets of instructions 522 embodying any one or more of the methodologies or functions described herein. The instructions 522 may also reside, completely or at least partially, within the main memory 504 and/or within the processing device 502 during execution thereof by the computer system 500, the main memory 504 and the processing device 502 also constituting computer-readable storage media.

The computer-readable storage medium 528 may also be used to store perfusion system controller 155 (as described with reference to the preceding figures), and/or a software library containing methods that call perfusion system controller 155. While the computer-readable storage medium 528 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any non-transitory medium that is capable of storing or encoding a set of instructions for execution by the machine and that can cause the machine to perform any one or more of the methodologies described herein. The term "non-transitory computer-readable storage medium" shall accordingly be taken to include, but not be limited to, solid-state memories, and optical and magnetic media.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "filtering", "mixing", "pumping", or the like, may refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present disclosure also relate to an apparatus for performing the operations herein. This apparatus may be specially constructed for the discussed purposes, and/or it may comprise a general purpose computer system selectively programmed by a computer program stored in the computer system. Such a computer program may be stored in a computer readable storage medium, such as, but not limited to, any type of disk including floppy disks, optical disks, CD-ROMs, and magnetic-optical disks, read-only memories (ROMs), random access memories (RAMs), erasable programmable read only memories (EPROMs), electrically erasable programmable read only memories (EEPROMs), magnetic disk storage media, optical storage media, flash memory devices, other type of machine-accessible storage media, or any type of media suitable for storing electronic instructions, each coupled to a computer system bus.

It is to be understood that the above description is intended to be illustrative, and not restrictive. Many other embodiments will be apparent to those of skill in the art upon reading and understanding the above description. Although the present disclosure has been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
   receiving a nutrient media solution into a closed-loop system comprising a sealed biological cell culture container, a filtering unit, a first fluid path between the sealed biological cell culture container and the filtering unit, and a second fluid path between the sealed biological cell culture container and the filtering unit, wherein the nutrient media solution is received through a semi-permeable membrane of the filtering unit;
   receiving an output of the sealed biological cell culture container at the filtering unit via the first fluid path, the output comprising beneficial molecules produced by a biological cell culture in the sealed biological cell culture container and waste products from the biological cell culture;
   filtering the output of the sealed biological cell culture container using the semi-permeable membrane to retain the beneficial molecules within the closed-loop system while removing the waste products;
   mixing the nutrient media solution with the filtered output of the sealed biological cell culture container;
   pumping a mixture of the nutrient media solution and the filtered output of the sealed biological cell culture container back to the sealed biological cell culture container through the second fluid path;
   receiving an instruction to provide a reward stimulus to a biological cell culture in the sealed biological cell culture container; and
   providing the reward stimulus to the biological cell culture.

2. The method of claim 1, wherein the closed-loop system further comprises a plurality of one-way valves, the method further comprising:
   controlling a direction of flow of the output of the sealed biological cell culture container and the mixture of the nutrient media solution and the filtered output of the sealed biological cell culture container using the plurality of one-way valves; and
   maintaining an approximately consistent flow rate through the closed-loop system.

3. The method of claim 1, wherein the nutrient media solution comprises at least one of a trophic growth hormone factor for the biological cell culture, a basal media, or a supplement.

4. The method of claim 3, wherein the trophic growth hormone factor comprises at least one of neurotrophins, ciliary neurotrophic factors (CNTF), glial cell line derived neurotrophic factors (GDNF), ephrins, epidermal growth factors (EGF), transforming growth factors (TGF), or neuron derived neurotrophic factors (NDNF).

5. The method of claim 3, wherein the basal media comprises at least one of an inorganic salt, an amino acid, an energetic substrate, a vitamin, a pH buffer, or a pH indicator.

6. The method of claim 3, wherein the supplement comprises at least one of a vitamin, a protein, a hormone steroid, a hormone thyroid, an essential fatty acid, a lipid, a sulfate mineral, an organic chemical compound, a monosaccharide, or a nucleotide.

7. The method of claim 1, further comprising:
measuring a temperature of at least one of the nutrient media solution, the output of the sealed biological cell culture container, or the mixture of the nutrient media solution and the filtered output of the sealed biological cell culture container;
responsive to detecting that the temperature falls below a low temperature threshold of a temperature range, heating at least one of the nutrient media solution, the output of the sealed biological cell culture container or the mixture of the nutrient media solution and the filtered output of the sealed biological cell culture container until the temperature is within the temperature range; and
responsive to detecting that the temperature exceeds a high temperature threshold of the temperature range, cooling at least one of the nutrient media solution, the output of the sealed biological cell culture container or the mixture of the nutrient media solution and the filtered output of the sealed biological cell culture container until the temperature is within the temperature range.

8. The method of claim 7, wherein the temperature range is between 36.5 degrees Celsius and 37.5 degrees Celsius.

9. The method of claim 1, wherein the biological cell culture comprises a neural culture, wherein the beneficial molecules comprise at least one of a growth factor or a hormone produced by the neural culture, wherein pores of the semi-permeable membrane are sized to permit passage of nutrients in the nutrient media solution and the waste products but to block passage of at least one of the growth factor or the hormone.

10. The method of claim 1, wherein the waste products leave the filtering unit via the semi-permeable membrane, and wherein the nutrient media solution enters the filtering unit via the semi-permeable membrane, via at least one of a diffusion process or an osmosis process.

11. A method comprising:
receiving a nutrient media solution into a closed-loop system comprising a biological cell culture, a sealed biological cell culture container, a filtering unit comprising a semi-porous membrane, a first fluid path between the sealed biological cell culture container and the filtering unit, and a second fluid path between the sealed biological cell culture container and the filtering unit;
receiving an output of the sealed biological cell culture container at the filtering unit via the first fluid path;
filtering the output of the sealed biological cell culture container;
mixing the nutrient media solution with the filtered output of the sealed biological cell culture container;
pumping a mixture of the nutrient media solution and the filtered output of the sealed biological cell culture container back to the sealed biological cell culture container through the second fluid path;
measuring electrical signals by the cells of the biological cell culture via one or more sensors, wherein the cells of the biological cell culture are disposed on a multi-electrode array (MEA) contained within the sealed biological cell culture container, the MEA comprising the one or more sensors; and
outputting a command, via a computer coupled to the MEA, to provide a reward stimulus to the contents of the sealed biological cell culture container responsive to a digital input signal from the MEA.

12. The method of claim 11, wherein the closed-loop system further comprises a plurality of one-way valves, the method further comprising:
controlling a direction of flow of the output of the sealed biological cell culture container and the mixture of the nutrient media solution and the filtered output of the sealed biological cell culture container using the plurality of one-way valves; and
maintaining an approximately consistent flow rate through the closed-loop system.

13. The method of claim 11, wherein the nutrient media solution comprises at least one of a trophic growth hormone factor for the biological cell culture, a basal media, or a supplement.

14. The method of claim 13, wherein the trophic growth hormone factor comprises at least one of neurotrophins, ciliary neurotrophic factors (CNTF), glial cell line derived neurotrophic factors (GDNF), ephrins, epidermal growth factors (EGF), transforming growth factors (TGF), or neuron derived neurotrophic factors (NDNF).

15. The method of claim 13, wherein the basal media comprises at least one of an inorganic salt, an amino acid, an energetic substrate, a vitamin, a pH buffer, or a pH indicator.

16. The method of claim 11, further comprising:
measuring a temperature of at least one of the nutrient media solution, the output of the sealed biological cell culture container, or the mixture of the nutrient media solution and the filtered output of the sealed biological cell culture container;
responsive to detecting that the temperature falls below a low temperature threshold of a temperature range, heating at least one of the nutrient media solution, the output of the sealed biological cell culture container or the mixture of the nutrient media solution and the filtered output of the sealed biological cell culture container until the temperature is within the temperature range; and
responsive to detecting that the temperature exceeds a high temperature threshold of the temperature range, cooling at least one of the nutrient media solution, the output of the sealed biological cell culture container or the mixture of the nutrient media solution and the filtered output of the sealed biological cell culture container until the temperature is within the temperature range.

17. The method of claim 11, wherein the output comprises beneficial molecules produced by the biological cell culture in the sealed biological cell culture container and waste products from the biological cell culture, wherein biological cell culture comprises a neural culture, wherein the beneficial molecules comprise at least one of a growth factor or a hormone produced by the neural culture, wherein the nutrient media solution is received through a semi-permeable membrane of the filtering unit, wherein pores of the semi-permeable membrane are sized to permit passage of nutrients in the nutrient media solution and the waste products but to block passage of at least one of the growth factor or the hormone.

18. The method of claim 1, wherein the reward stimulus comprises a chemical reward stimulus, and wherein the chemical reward stimulus is injected into the second fluid path of the closed-loop system.

* * * * *